United States Patent [19]
Roedern et al.

[11] Patent Number: 5,556,836
[45] Date of Patent: Sep. 17, 1996

[54] USE OF D-GLUCOPYRANURONIC ACIDS AND THEIR DERIVATIVES FOR INCORPORATION IN PHARMACOLOGICALLY ACTIVE PEPTIDES AND THEIR SALTS

[75] Inventors: Erich G. Roedern, Bad Soden-Salmunster; Horst Kessler, Schwalbach; Bernhard Kutscher, Maintal; Michael Bernd, Frankfurt; Thomas Klenner, Hirschberg, all of Germany

[73] Assignee: Asta Medica Aktiengesellschaft, Dresden, Germany

[21] Appl. No.: 332,071

[22] Filed: Nov. 1, 1994

[30] Foreign Application Priority Data

Nov. 8, 1993 [DE] Germany .......................... 43 38 015.8

[51] Int. Cl.$^6$ .......................... A61K 38/09; A61K 38/14; C07H 15/04; C07K 9/00
[52] U.S. Cl. .................. 514/15; 514/8; 530/313; 530/322; 530/332; 530/333; 536/17.9; 930/30; 930/130
[58] Field of Search ................ 514/2, 8, 12, 15; 530/313, 322, 323, 332, 333; 536/17.2, 17.9, 18.2, 18.6, 18.7, 29.1, 55, 55.2, 55.3; 930/30, 130

[56] References Cited

U.S. PATENT DOCUMENTS 4,360,663 11/1982 Asano et al. ..................... 536/5

FOREIGN PATENT DOCUMENTS 0417454 3/1991 European Pat. Off. .
0450461 10/1991 European Pat. Off. .
WO91/04247 4/1991 WIPO .
WO92/08733 5/1992 WIPO .

OTHER PUBLICATIONS

Yoshikawa et al., "Chemical & Pharmaceutical Bulletin", Pharmaceutical Society of Japan, vol. 29, No. 9, Sep. 1981.

Chemische Berichte, vol. 89, No. 3, issued 1956, Fodor et al, "Die Raumstruktur der Aminodesoxyzucker . . . ", pp. 701–708.

Chemische Berichte, vol. 108, issued 1975, Fuchs et al, "Synthese von 7-Amino-2, 6-anhydro-7-desoxy-D-glycero . . . ", pp. 2254–2260.

Chemische Berichte, vol. 88, No. 2, issued 1955, Heyns et al, "Synthese der D-Glucosaminouronsaure . . . ", pp. 188–195.

Angew, Chem. Int. Ed. Engl., vol. 33, No. 6, issued 1994, Roedern et al, "A Sugar Amino Acid as a Novel Peptidomimetic", pp. 687–689.

J. Am. Chem. Soc., vol. 114, issued 1992, Sakai et al, "Total Synthesis of Galantin I . . . ", pp. 998–1010.

J. Inorg. Biochem., vol. 41, issued 1991, Whitfield et al, "Metal Binding to Heparin Monosaccharides . . . ", pp. 157–170.

*Primary Examiner*—Jeffrey E. Russel
*Attorney, Agent, or Firm*—Cushman Darby & Cushman

[57] ABSTRACT

Use of 7-amino-L-glycero-L-gulo-2,6-anhydro-7-desoxy-heptonic acid and 2-benzoxycarbonylamino-0$^1$-methyl-2-desoxy-β-glucopyranuronic acid, their derivatives and the enantiomorphous compounds for incorporation and for manufacture in pharmacologically active peptide hormones.

15 Claims, No Drawings

USE OF D-GLUCOPYRANURONIC ACIDS AND THEIR DERIVATIVES FOR INCORPORATION IN PHARMACOLOGICALLY ACTIVE PEPTIDES AND THEIR SALTS

The invention relates to 7-amino-L-glycero-L-gulo-2,6-anhydro- 7-desoxy-heptonic acid, a multi-stage process for manufacture and the use of the compound and the enantiomorphous 7-amino-D-glycero-D-gulo-2,6-anhydro-7-desoxy-heptonic acid for incorporation in pharmacologically active peptide hormones.

In addition the invention relates to 2-benzoxycarbonylamino- $O^1$-methyl-2-desoxy-β-D-glucopyranuronic acid and the use of the compound and the enantiomorphous 2-benzoxycarbonylamino- $O^1$-methyl-2-desoxy-β-D-glucopyranuronic acid for incorporation in pharmacologically active peptide hormones.

In particular, the invention relates to A compound comprising a D-glucopyranuronic acid having the formula:

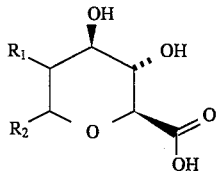

where $R^1$ signifies OH, $NH_2$, $NH-CO-O-CH_2-C_6H_5$, $NH-CO-O$-tert.butyl, or $NH-CO-CH_3$, $R^2$ signifies $CH_2-NH_2$, OH, $OCH_3$, $OCH_2-C_6H_5$, $CH_2-NH-CO-O-CH_2-C_6H_5$, $CH_2-NH-CO-O$-tert.butyl or $CH_2-NH-CO-CH_3$, or its enantiomer incorporated into a pharmacologically active peptide or its salt.

The invention also relates to methods for manufacturing 7-amino-L-glycero-L-gulo-2,6-anhydro-7-desoxy-heptonic acid comprising the steps of:

a) reducing β-D-glucopyranosyl nitromethane with hydrogen on a palladium catalyst and then reacting resulting reduced β-D-glucopyranosyl nitromethane with chloroformic acid benzyl ester;

b) oxidizing N-benzoxycarbonyl-β-D-glucopyranosyl methylamine with oxygen on a platinum catalyst and then esterifying resulting oxidized N-benzoxycarbonyl-β-D-glucopyranosyl methylamine with alcohol;

c) and splitting protective groups of the 7-benzoxycarbonylamino-L-glycero-L-gulo- 2,6-anhydro-7-desoxy-heptonic acid methyl ester formed as a result of steps a) and b).

Numerous biologically active peptides have been discovered and characterised in the last twenty or thirty years. As neurotransmitters, neuromodulators and hormones, they influence, after binding to their membrane-based receptors, the inter-cell communication and control a number of vital functions such as metabolism, immune defence, digestion, breathing, pain sensation etc.. Because of their wide-ranging functions they are of great medical interest, so that the number of native and modified peptides which are used as drugs is growing the whole time. Of particular interest is the possibility, by the incorporation or by the replacement of individual amino acids in the peptide chain, of changing the conformational and biological parameters.

The peptides modified in this way can exhibit altered biochemical and pharmacological properties (A. Glannis, T. Kolter, Angew. Chem. 1993, 105 1303). For the design of modified peptides, carbohydrates possess the advantage of structural diversity and physiological innocuousness. By the incorporation of specific sugar molecules in peptide hormones, the pharmacological activity of the latter can be altered considerably.

The subject of the invention is the preparation of the novel sugar amino acid 7-amino-L-glycero-L-gulo-2,6-anhydro-7-desoxy-heptonic acid.

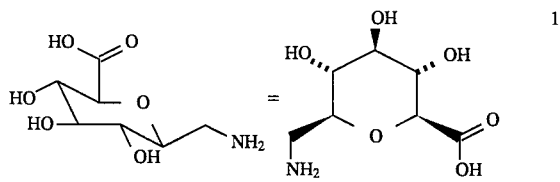

The compound possesses as a structural feature the rigid, pyranoid backbone of sugar. The latter limits the conformation of peptides. The free hydroxyl groups enhance the hydrophilic properties of the peptides, on the other hand the contrary effect can easily be achieved by the use of non-polar protective groups. Whereas pyranoid rings are frequently present in therapeutically relevant natural substances, such a structural feature within a peptide chain is known only for the case of galatinic acid, which is a constituent of the natural peptide galatin I (N. Sakai, Y. Ohfume, J. Am. Chem. Soc. 1992, 114 998–1010).

The sugar amino acid 7-amino-L-glycero-L-gulo-2,6-anhydro- 7-desoxy-heptonic acid is obtainable in four stages from D-glucose in a total yield of 12%.

By the condensation of nitromethane on glucose, the nitro compound 2 is obtained in a manner known per se (L. Petrus, S. Bystricky, T. Sticzay, V. Bilik, Chem. zvesti 1982, 36(1) 103–110). The latter is reduced quantitatively to the amine with hydrogen on a palladium catalyst, and afterwards the amino group is protected by reacting with chloroformic acid benzyl ester through the introduction of the benzyloxy-carbonyl group. By selective oxidation of the compound 3 with oxygen on a platinum catalyst, the primary hydroxy group is oxidized to the carboxylic acid and afterwards reacted with methanol to the methyl ester 4. The free amino acid 1 can be obtained in crystalline form by removal of the protective groups in a manner known per se.

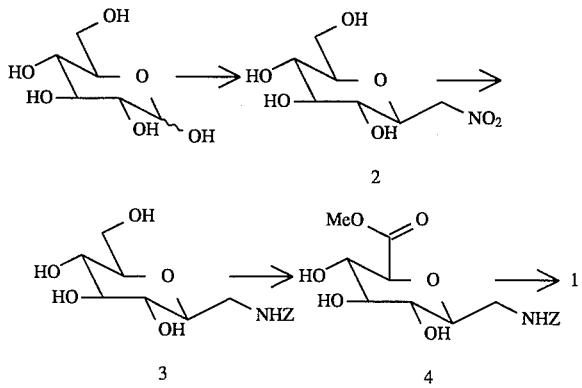

$Z=C_6H_5-CH_2-O-CO-$

The inexpensive starting materials and the recyclable palladium and platinum catalysts make synthesis on a commercial scale possible.

The enantiomorphous sugar amino acid 7-amino-D-glycero-D-gulo- 2,6-anhydro-7-desoxy-heptonic acid is known from the literature (E. F. Fuch, J. Lehmann (Chem. Ber. 108 (1975) 2254).

The synthesis of the compound likewise takes place starting from D-glucose, but very expensively in ten stages. No information is given on the possible use of this compound as a peptide structural element.

In addition, the two sugar amino acids 2-benzoxycarbonylamino- $O^1$-methyl-2-desoxy-α-D-glucopyranuronic acid 5 and 2-benzoxycarbonylamino-$O^1$-methyl-2-desoxy-β-D-glucopyranuronic acid 6 and/or their unprotected derivatives can be incorporated in pharmacologically active peptides.

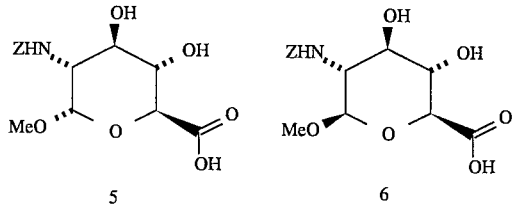

The compound 5 is known from the literature (K. Heyns, H. Paulsen, Chem. Ber. 1953, 88, 188–195), but no information is given on a possible use of the compound.

The novel compound 6 can be manufactured starting from 2-amino-$O^1$-methyl-2-desoxy-Tri-$O^3$,$O^4$,$O^6$-acetyl-β-D-gluco pyranoside hydrobromide 8 (G. Fodor, L. Ötvös, Chem. Ber., 1955, 89, 701–708). By reacting with chloroformic acid benzyl ester and subsequent reaction with dimethyl ethyl amine in methanol, 2-benzyloxy-carbonylamino-$O^1$-methyl-2-desoxy-β-D-glucopyranoside 7 is obtained.

The oxidation of the compound 7 with oxygen on a platinum catalyst finally produces 2-benzoxycarbonylamino-$O^1$-methyl- 2-desoxy-β-D-glucopyranuronic acid 6

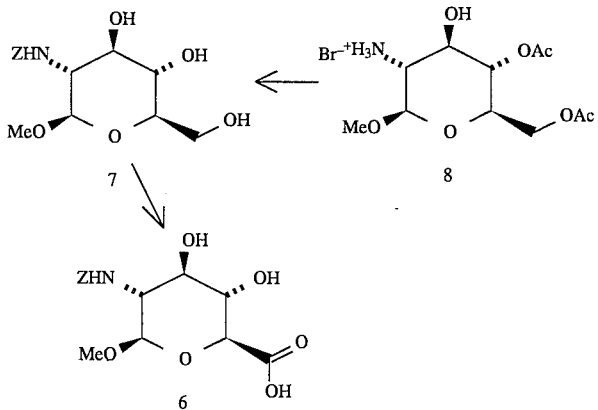

The enantiomorphous sugar amino acids can be used as amino acid substitutes within the peptide chain, so that novel derivatized peptide hormones with both agonistic and antagonistic properties can also be manufactured.

7-amino-L-glycero-L-gulo-2,6-anhydro-7-desoxy-heptonic acid can for example be incorporated in cyclic hexapeptides in such a way that one or two adjoining amino acids are replaced respectively. The following cyclic peptides have been manufactured, which exhibit an activity as somatostatin analogs (See SEQUENCE ID NOs:1 and 2, respectively):

cyclo(—Zu$^1$—Tyr$^2$—D—Trp$^3$—Lys$^4$—Val$^5$)  D-22475
cyclo(—Zu$^1$—Phe$^2$—D—Trp$^3$—Lys$^4$—Thr$^5$)  D-22402

Zu=7-amino-L-glycero-L-gulo-2,6-anhydro-7-desoxy-heptonic acid

The peptides are derived from cyclic somatostatin analogs (D. F. Veber, Peptides, Chemistry and Biology, Proc. of the Twelfth American Peptide Symposium (Ed.: J. A. Smith, J. E. Rivier), Escom, Leiden, 1992, pp. 3–14), which are cyclized, instead of via Zu, via the amino acids -Pro-Phe- or a cystine-disulphide bridge.

7-amino-L-glycero-L-gulo-2,6-anhydro-7-desoxy-heptonic acid can also be incorporated in long-chain non-cyclic peptides. For example, the following LH-RH (Luteinizing Hormone Releasing Hormone (See SEQUENCE ID NO: 3) antagonist can be obtained.

Ac—D—(2-NaL)-p-Cl—D—Phe—D—(3-Pal)—Ser—Tyr—D—Lys—(Zu)—Leu—Arg—Pro—D—AlaNH$_2$ × TFA D-22620

Zu=7-amino-L-glycero-L-gulo-2,6-anhydro-7-desoxy-heptonic acid

TFA=trifluoroacetate

This antagonist shows a persistent testosterone suppression in the dosage 0.5–1.5 mg/kg in the animal test on rats.

By the incorporation of the protected sugar amino acid 7-benzoxycarbonylamino-L-glycero-L-gulo- 2,6-anhydro-7-desoxyheptonic acid methyl ester in the LHRH agonists derived from nafarelin, pGlu-His-Trp-Ser-Zu-Leu-Arg-Pro-Gly-NH$_2$(See SEQUENCE ID NO: 4)×2 TFA D-22677 can for example be obtained.

By the incorporation of the above-mentioned protected sugar amino acid in the LHRH antagonists derived from cetrorelix, Ac-D- (2-Nal)-p-Cl-D-Phe-D-(3-Pal) -Ser-Tyr-Zu-Leu-Arg(TFA)-Pro-D-Ala-NH$_2$(See SEQUENCE ID NO: 5) D-23010 and Ac-D-(2-Nal)-p-Cl-D-Phe-D-(3-Pal) -Ser-Zu-Leu-Arg(TFA)-Pro-D-Ala-NH$_2$(See SEQUENCE ID NO: 11) ER 133 can be obtained.

During the incorporation in peptides and in their salts the pharmacological effectiveness can be controlled by the use of more hydrophilic or more strongly hydrophobic protective groups in the novel sugar amino acid. Thus it is possible, for example, to manufacture by acetylation 7-acetylamino-L-glycero-L-gulo- 2,6-anhydro-7-desoxy-heptonic acid methyl ester, which can likewise be incorporated in peptides.

Preparation of β-D-glucopyranosyl nitromethane (2)

50 g of moisture-free D-glucose are dissolved in 200 ml dimethyl sulphoxide and 100 ml methanol. 100 ml nitromethane and a suspension of 30 g sodium methylate in 320 ml methanol are added to the latter and stirring takes place for 24 hours at room temperature. 250 ml n-butanol are added to the reaction mixture and stirred for 1 hour at 0° C. The latter is then filtered and the residue washed with 100 ml isopropanol and 100 ml diethyl ether. After drying, 71 g of a bright yellow powder are obtained. The latter is dissolved in 200 ml water and passed through a column with 100 g of cation exchanger (Aldrich, Amberlyst 15, strongly acid H$^+$ form). The ion exchanger is washed with 500 ml water. The aqueous, red solution is concentrated to 100 ml and heated to 90 °C. over 30 hours. 2 g of fine activated carbon are added to the hot solution, which is then stirred for 10 minutes, filtered through 5 g kieselguhr and rewashed with 200 ml water.

150 g of anion exchanger (Fluka, Amberlyst A-26, strongly basic OH$^-$ form) are added to the solution and stirred for 1 hour. The latter is filtered and the ion exchanger washed with 3–5 l water. The ion exchanger is thereupon added to 400 ml water, into which carbon dioxide gas is introduced for 30 minutes in order to release the product. The ion exchanger is filtered off and washed with 1000 ml water.

The filtrate is concentrated under vacuum to 30 ml and freeze-dried. The hard foam obtained in this way is recrystallized several times from acetone. 19.3 g of product are obtained as a colourless powder. (Melting point: 175° C. $[\alpha_D]=+9.1°$). Lit.: L. Petrus, S. Bystricky, T. Sticzay, V. Bilik, Chem. zvesti 1982, 36 (1), 103–110.

Preparation of N-benzyloxycarbonyl-β-D-glucopyranosyl-methylamine (3)

5 g of β-D-glucopyranosyl nitromethane (2) are dissolved in 80 ml methanol and 20 ml water, 3 g of palladium catalyst (Degussa, Pd-C 10%, approx. 50% water) are added and stirring takes place for 24 hours under hydrogen atmosphere (hydrogen consumption approx. 3.5 l). The catalyst is filtered off and washed with a mixture of 80 ml water and 20 ml methanol. To this solution are added 10.5 g sodium hydrogen-carbonate and 17 ml chloroformic acid benzyl ester, followed by vigorous stirring for 1 hour. 50 ml water are added to the reaction mixture and the methanol is removed under vacuum. The aqueous solution is washed three times with 20 ml diethyl ether on each occasion and evaporated to dryness under vacuum (bath temperature 40° C.). The residue is absorbed in 80 ml acetone. The inorganic salts are filtered off and washed in portions with 80 ml acetone. The acetone is distilled off under vacuum, after the drying 7.21 g of thin-layer chromatographically identical product are obtained as a colourless hard foam.

Preparation of 7-benzyloxycarbonylamino-L-glycero-L-gulo- 2,6-anhydro-7-desoxy-heptonic acid methyl ester (4)

5 g of (N-benzoxycarbonyl)-β-D-glucopyranosyl methylamine (3) are dissolved in 100 ml water and 5 g of platinum catalyst (Degussa, Pt-C 10%, approx. 50% water, activation by boiling glacial acetic acid) added.

A strong oxygen current is introduced at 90 °C. for 36 hours with stirring. The pH value is held between 7 and 8 by the hourly addition of 10% sodium hydrogen carbonate solution.

2 g of platinum catalyst are added once again after 8 and 18 hours respectively. The catalyst is filtered off and washed with 30 ml water. To the aqueous solution are added 10 g of cation exchanger (Aldrich, Amberlyst 15, strongly acid, H$^+$ form) and stirring takes place for 10 minutes. The ion exchanger is filtered off and washed with water, the filtrate concentrated under vacuum and freeze-dried. The powdery residue is dissolved in 100 ml absolute methanol, 2.9 g dicyclohexyl carbodiimide and 0.2 g 4-(dimethylamino)-pyridine are added, followed by stirring for a further 2 hours under vacuum. Evaporation almost to dryness takes place and the resulting syrup is purified chromatographically on silica gel (100 g silica gel, mobile solvent chloroform-:methanol/9:1). The mobile solvent is distilled off from the product fraction, the hard foam obtained recrystallized from water. 1.9 g of thin-layer chromatographically identical product are obtained in the form of colourless needles (melting point: 164 °C., $[\alpha]_D=-21.7°$).

Preparation of 7-amino-L-glycero-L-gulo-2.6-anhydro-7-desoxy-heptonic acid (1)

0.1 g of the protected amino acid 4 are dissolved in 2 ml methanol, 0.4 ml 1N sodium hydroxide solution are added and stirred for 5 minutes.

After the addition of 0.3 g of cation exchanger (Aldrich, Amberlyst 15, strongly acid, H$^+$ form) stirring takes place for a further 5 minutes, the ion exchanger is filtered off and washed with 2 ml methanol. 0.1 g of palladium catalyst (Degussa, Pt-C 10%, approx. 50% water) are added to the filtrate, followed by stirring for 4 hours under hydrogen atmosphere.

The catalyst is filtered off, washed with 2 ml water and 2 ml methanol, and the solvent removed under vacuum. After drying 0.5 g of product are obtained as a colourless powder (melting point >260° C., $[\alpha]_D=-41.2°$).

N-acetyl-β-D-glucopyranosyl methylamine 3.5 g of β-D-glucopyranosyl nitromethane (2) are dissolved in 80 ml MeOH and 20 ml H$_2$O, 3 g of Pd catalyst (Degussa, Pd-C 10%, approx. 50% H$_2$O) are added and stirred in an autoclave for 24 hours under 50 bar H$_2$ atmosphere (H$_2$ consumption approx. 3.5 l). The catalyst is filtered off and washed with a mixture of 80 ml H$_2$O and 20 ml MeOH and the solvent removed under vacuum. The residue is absorbed in 50 ml abs. MeOH and mixed with 1.6 ml acetic anhydride and stirred for 5 min and the solvent removed under vacuum. The residue is chromatographed on silica gel (mobile solvent CHCl$_3$: MeOH 4:1). After the drying 3.5 g (95%) of product are obtained as a colourless foam.

7-acetylamino-L-glycero-L-gulo-2.6-anhydro-7-desoxy-heptonic acid methyl ester 3 g of N-acetyl-β-D-glucopyranosyl methylamine are dissolved in 100 ml H$_2$O and 1.5 g of Pt catalyst (Degussa, Pt-C 10%, approx. 50% H$_2$O, activation by short ultrasonic treatment) added. At 90° C. a strong O$_2$ current is introduced over 22 hours with stirring. The latter is pumped in a circle by means of a pump in the sealed apparatus. The pH value is held between 7 and 8 by the hourly addition of 10% NaHCO$_3$ solution. 0.5 of freshly activated Pt catalyst are added once again after 8 hours and 18 hours respectively.

On completion of the oxidation the catalyst is filtered off, 10 g of cation exchanger (Aldrich, Amberlyst 15, strongly acid, H$^+$ form) are added to the filtrate and stirring for 10 minutes follows. The ion exchanger is filtered off and washed, the filtrate concentrated under vacuum and freeze-dried. The powdery residue is dissolved in 100 ml abs. MeOH, 2.5 g DCC and 0.2 g 4-(dimethylamino)pyridine are added and stirring for 0.5 hours follows. The urea derivative precipitating is filtered off and washed with MeOH, the filtrate is evaporated almost to dryness under vacuum and the resulting syrup purified by thin-layer chromatography on silica gel (100 g silica gel, mobile solvent CHCl$_3$: MeOH/ 6:1). 1.1 g (34%) of a thin-layer chromatographically identical product are obtained in the form of a colourless foam.

The manufacture of 2-amino-0$^1$-methyl-2-desoxy-tri-0$^3$, 0$^4$,0$^6$-acetyl-β-D-glucopyranoside hydrobromide 8 takes place according to the instructions of G. Fodor, L. Ötvös, Chem. Ber., 1955, 89, 701–708.

2-benzyloxycarbonylamino-0$^1$-methyl-2-desoxy-β-D-glucopyranoside 7

56 g (0.66 mol) of $NaHCO_3$ are dissolved in a 2 l separatory funnel, covered with a layer of 700 ml ethyl acetate and added to 70 ml (0.21 mol) of a 50% solution of chloroformic acid benzyl ester in toluene. 56 g (0.14 mol) of 2-amino- $O^1$-methyl-2-desoxy-tri-$O^3,O^4,O^6$-acetyl-α-D-glucopyranoside hydrobromide 8 are dissolved in 100 ml $H_2O$ and added carefully to this mixture. The whole is shaken carefully and when $CO_2$ evolution is no longer detectable shaken for a further 5 min. The aqueous phase is separated off, the organic phase washed once with 100 ml $H_2O$, three times with 100 ml 1.0 HCl and three times with 100 ml $H_2O$ respectively.

The organic phase is dried with $MgSO_4$ and the solvent removed completely under vacuum. 62 g of colourless platelets are obtained, which are dissolved in 150 ml abs. MeOH, to which 20 ml dimethyl ethyl amine are added and the whole left to stand overnight. The solvent is removed under vacuum and recrystallized out of water. 44 g (96%) of 2-benzyloxycarbonylamino- $O^1$-methyl-2-desoxy-β-D-glucopyranoside 7 are obtained as fine colourless needles.

2-benzoxycarbonylamino-$O^1$-methyl-2-desoxy-β-D-glucopyranuronic acid 6

10 g of 2-benzyloxycarbonylamino-$O^1$-methyl-2-desoxy-β-D-glucopyranoside 7 are dissolved in 100 ml $H_2O$ and 5 g of Pt catalyst (Degussa, Pt-C 10%, approx. 50% $H_2O$, activation by short ultrasonic treatment) added. At 85° C. a strong $O_2$ current is introduced over 50 hours with stirring. The latter is pumped in a circle by means of a pump in the sealed apparatus. The pH value is held between 7 and 8 by the hourly addition of 10% $NaHCO_3$ solution. 2 freshly activated Pt catalysts are added once again after 15 hours and 30 hours respectively. On completion of the oxidation the catalyst is filtered off, 20 g of cation exchanger (Aldrich, Amberlyst 15, strongly acid, $H^+$ form) are added to the filtrate and stirring for 10 minutes follows. The ion exchanger is filtered off and washed with water, the filtrate concentrated under vacuum to approx. 30 ml, wherein 5.2 g (54%) of 2-benzoxycarbonylamino-$O^1$-methyl-2-desoxy-β-D-glucopyranuronic acid 6 crystallize out in the form of colourless fine needles (melting point: 142° C.).

Preparation of cyclo(-$Zu^1$-$Phe^2$-D-$Trp^3$-$Lys^4$-$Thr^5$) D-22402

The synthesis was carried out in liquid phase. In the case of the peptide couplings the activation was performed with EDCI (1-ethyl-3-(3'-dimethylaminopropyl)carbodiimide/HOBT (N-hydroxybenzotriazole), the cyclization with TBTU (2-(1H-benzotriazol-1yl)- 1,1,3,3-tetramethyl uroniumtetrafluoroborate). The protected sugar amino acid 4 is abbreviated to Z-Zu-OMe.

Manufacture of the starting compounds

Boc-Lys(Z)-Thr-OMe 1.14 g (3 mmol) of Boc-Lys(Z)-OH, 0.51 g (3 mmol) of H-Thr-OMe.HCl, 0.68 g of (3.6 mmol) of EDCI, 0.58 g (3.6 mmol) of HOBT and 0.66 ml (6 mmol) of NMM are dissolved at −10° C. in 10 ml THF and stirred at room temperature for 15 hours. The THF is distilled off under vacuum, the residue dissolved in 50 ml ethyl acetate and the organic phase washed three times with 10 ml 0.5 N HCl, 10% $NaHCO_3$ solution and water respectively. The organic phase is dried with $MgSO_4$ and the solvent distilled off under vacuum. 1.36 g (92%) of thin-layer chromatographically identical Boc-Lys(Z)-Thr-OMe are obtained as a colourless foam.

Z-Phe-D-Trp-OMe 0.60 g (2 mmol) of Z-Phe-OH, 0.51 g (2 mmol) of H-D-Trp-OMe.HCl, 0.46 g (2.4 mmol) of EDCI, 0.32 g (2.4 mmol) of HOBT and 0.44 ml (4 mmol) of NMM are dissolved at −10° C. in 10 ml THF and stirred at room temperature for 15 hours. The THF is distilled off under vacuum, the residue dissolved in 50 ml ethyl acetate and the organic phase washed three times with 10 ml 0.5 N HCl, 10% $NaHCO_3$ solution and water respectively. The organic phase is dried with $MgSO_4$ and the solvent distilled off under vacuum. 0.48 g (48%) of thin-layer chromatographically identical Z-Phe-D-Trp-OMe are obtained as a colourless powder.

Boc-Lys(Z)-Thr-Zu-OMe 0.5 g (1 mmol) of Boc-Lys(Z)-Thr-OMe are dissolved in a mixture of 5 ml THF and 5 ml MeOH. While stirring 1.2 ml (1.2 mmol) of a 1N NaOH are added and stirred for 2 minutes. The reaction mixture is neutralized with 0.22 g (1.5 mmol) HOBT.

0.35 g (1 mmol) of Z-Zu-OMe are dissolved in 5 ml MeOH, 50 mg of 10% Pd/C catalyst added and hydrated at room temperature with stirring under a hydrogen atmosphere for 0.5 hours. The catalyst is filtered off and washed with 5 ml MeOH. The filtrate is added to the neutralized reaction mixture from the saponification and the solvent is removed under vacuum. The residue is dissolved in a mixture of 3 ml DMF and 3 ml THF and at −10° C. 0.3 g (1.5 mmol) EDCI and 0.165 ml (1.5 mmol) NMM are added. After 15 hours the reaction is concluded by the addition of 5.0 g of mixed-bed ion exchanger (Merck ion exchanger V), and stirring for 0.5 hours follows. The ion exchanger is filtered off and washed with MeOH, the filtrate concentrated under vacuum and chromatographed on silica gel (mobile solvent $CHCl_3$: MeOH, 4:1, V:V).

0.43 g (63%) of thin-layer chromatographically identical Boc-Lys(Z)-Thr-Zu-OMe are obtained as a colourless oil.

Boc-Lys (Z) -Thr-Zu-Phe-D-Trp-OMe (See SEQUENCE ID NO: 6)0.43 g (0.63 mmol) of Boc-Lys(Z)-Thr-Zu-OMe are dissolved in a mixture of 5 ml THF and 5 ml MeOH. While stirring 0.8 ml (0.8 mmol) of a 1N NaOH are added and stirred for 2 minutes. The reaction mixture is neutralized with 0.15 g (1.0 mmol) HOBT.

0.40 g (0.8 mmol) of Z-Phe-D-Trp-OMe are dissolved in 5 ml MeOH, 50 mg of 10% Pd/C catalyst added and hydrated at room temperature with stirring under a hydrogen atmosphere for 0.5 hours. The catalyst is filtered off and washed with 5 ml MeOH. The filtrate is added to the neutralized reaction mixture from the saponification and the solvent is removed under vacuum. The residue is dissolved in a mixture of 3 ml DMF and 3 ml THF and at −10° C. 0.2 g (1.0 mmol) EDCI and 0.165 ml (1.5 mmol) NMM are added. After 15 hours the reaction is concluded by the addition of 5.0 g of mixed-bed ion exchanger (Merck ion exchanger V) and stirring takes place for 0.5 hours. The ion exchanger is filtered off and washed with MeOH, the filtrate concentrated under vacuum and chromatographed on silica gel (mobile solvent $CHCl_3$: MeOH, 9:1, V:V) and freeze-dried from water/t-butanol. 0.51 g (80%) of thin-layer chromatographically identical Boc-Lys(Z)-Thr-Zu-Phe-D-Trp-OMe are obtained as a colourless powder.

cyclo(-$Zu^1$-$Phe^2$-D-$Trp^3$-$Lys^4$-$Thr^5$)

0.2 g (0.2 mmol) of Boc-Lys(Z)-Thr-Zu-Phe-D-Trp-OMe are dissolved in 2 ml MeOH and 1 ml THF, 0.25 ml (0.25 mmol) 1N NaOH are added and stirred for 3 minutes. 200 mg of strongly acid cation exchanger (Amberlyst 15, $H^+$ form) are added, followed by stirring for 5 minutes.

The cation exchanger is filtered off and washed with 5 ml MeOH. The filtrate is concentrated under vacuum and dried over $P_2O_5$ under high vacuum. The substance is taken up in 3 ml abs. THF, mixed with 0.1 ml methanethiol and 1 ml HCl/diethyl ether (abs. diethyl ether is for this saturated with hydrogen chloride at 0° C.) and the reaction mixture is treated ultrasonically for 1 minute. After 5 minutes the solvent is removed under vacuum and dried under high vacuum. A slightly yellowish solid is obtained, which is dissolved in 100 ml distilled DMF. To this are added 40 µl water, 40 mg (0.25 mmol) HOBT, 100 mg (0.25 mmol) TBTU and 170 µl DIPEA. After 0.5 hours of stirring at room temperature the solvent is removed under vacuum, and the residue chromatographed on silica gel (mobile solvent $CHCl_3$: MeOH, 9:1, V:V) and thereupon purified by HPLC. The white solid so obtained in dissolved in 2.5 ml MeOH, 10 mg 10% Pd/C catalyst are added and hydrated at room temperature with stirring under a hydrogen atmosphere for 20 minutes. The catalyst is filtered off and washed with 2 ml MeOH. The solvent is distilled off under vacuum and freeze-dried. 82 mg (54%) of HPLC-pure cyclo(-Zu-Phe-D-Trp-Lys-Thr) are obtained as a colourless powder, FAB-MS: m/z 753 ($M+H^+$).

The manufacture of cyclo (-Zu1-Tyr$^2$-D-Trp$^3$-Lys$^4$-Val$^5$) D-22475 takes place in a similar manner. FAB-MS: m/z 767 ($M+H^+$).

Preparation of Ac-D-(2-Nal)-p-Cl-D-Phe-D-(3-Pal)-Ser-Tyr-D-Lys(Zu)-Leu-Arg-Pro-D-AlaNH$_2$-TFA D-22620

78 mg (0.22 mmol) of 7-benzyloxycarbonylamino-L-glycero-L-gulo- 2,6-anhydro-7-desoxy-heptonic acid methyl ester are dissolved in 2 ml MeOH and saponified by the addition of 0.23 ml 1N NaOH.

After 5 minutes 100 mg of cation exchanger (Aldrich, Amberlyst 15, strongly acid, $H^+$ form) are added and stirred for a further 5 minutes. The ion exchanger is filtered off and washed with 5 ml MeOH. The filtrate is concentrated under vacuum to a syrup. The latter is absorbed in a mixture of 0.5 ml DMF and 0.5 ml THF and to this are added 280 mg (0.2 mmol) D-22516, 52 mg (0.25 mmol) DCC and 0.022 ml (0.2 mmol) N-methyl morpholine. After 12 hours of stirring at room temperature the reaction mixture is added with ultrasonic treatment to 20 ml ether. The colourless precipitate is filtered off, washed with ether and dissolved in a mixture of 10 ml MeOH and 40 ml water. The urea derivative remains undissolved and is filtered off. The filtrate is evaporated to dryness under vacuum and dissolved in 17 ml MeOH. This solution is separated into 2 ml portions by RP chromatography (MPLC 30 bar, 50 g RP-Eurosil-gel, flow 10 ml/min, MeOH/$H_2O$ with 0.1% TFA, gradient 55% MeOH to 70% MeOH in 40 min). The product is precipitated out of ether-hexane after the separation. 100 mg (0.054 mmol, 27%) of product are obtained as trifluoroacetate in the form of a colourless powder. FAB-MS: 1724.5 ($M+H^+$), relative molecular mass given above - TFA.

The manufacture of the starting compound D-22516=Ac-D-NaL-(2)-D-Phe(4Cl)-D-Pal(3)-Ser-Tyr-D-Lys-Leu-Arg-Pro-D-AlaNH$_2$ is given in the patent application of Schally et al., PCT WO 92/13883 on page 33 ff.

Preparation of the LHRH agonist pGlu-His-Trp-Ser-Zu-Leu-Arg-pro-Gly-NH$_2$.2 TFA (See SEQUENCE ID NO: 7) D-22677 derived from nafarelin The synthesis is carried out in liquid phase. The peptide couplings are activated with EDCI/HOBT. The protected sugar amino acid 7-benzyloxycarbonylamino-L-glycero-L-gulo-2-6-anhydro- 7-desoxy-heptonic acid methyl ester is abbreviated to Z-Zu-OMe.

Synthesis strategy:

pGlu—His(Trt)/Trp—Ser/Zu—Leu/Arg(Pmc)/Pro—Gly—NH$_2$
Trp—Ser—Zu—Leu/Arg(Pmc)—Pro—Gly—NH$_2$
Trp—Ser—Zu—Leu—Arg(Pmc)—Pro—Gly—NH$_2$ (See SEQUENCE ID NO: 12)
pGlu—His(Trt)—Trp—Ser—Zu—Leu—Arg(Pmc)—Pro—Gly—NH$_2$ (See SEQUENCE ID NO: 8)
pGlu—His—Trp—Ser—Zu—Leu—Arg—Pro—Gly—NH$_2$ (See SEQUENCE ID NO: 8)

pGlu—His(Trt)—OMe 0.39 g (3 mmol) of pGlu-OH, 1.34 g (3 mmol) of H-His-Trt-OMe.HCl, 0.68 g (3.6 mmol) of EDCI, 0.58 g (3.6 mmol) of HOBT and 0.66 ml (6 mmol) of NMM are dissolved at −10° C. in 8 ml DMF and stirred at room temperature for 15 hours. The DMF is distilled off under vacuum, the residue dissolved in 50 ml ethyl acetate and the organic phase washed three times with 10 ml 0.5 N HCl, 10% NaHCO$_3$ solution and $H_2O$ respectively. The organic phase is dried with MgSO$_4$ and the solvent distilled off under vacuum and the crude product so obtained chromatographed on silica gel (mobile solvent $CHCl_3$: MeOH 9:1 V=V). 0.72 g (46%) of thin-layer chromatographically identical pGlu-His(Trt)-OMe are obtained as a colourless hard foam.

2-Trp-Ser-OMe 3.38 g (10 mmol) of Z-Trp-OH, 1.55 g (10 mmol) of H-Ser-OMe.HCl, 2.00 g (10 mmol) of EDCI, 1.50 g (10 mmol) of HOBT and 3.3 ml (10 mmol) of NMM are dissolved at −10° C. in 50 ml THF and stirred at room temperature for 15 hours. The THF is distilled off under vacuum, the residue dissolved in 50 ml ethyl acetate and the organic phase washed three times with 10 ml 0.5 N HCl, 10% NaHCO$_3$ solution and $H_2O$. The organic phase is dried with MgSO$_4$ and the solvent distilled off under vacuum.

The residue is taken up in 2-propanol, in the course of which the product precipitates. The latter is filtered off and dried. 2.90 g (68%) of thin-layer chromatographically identical Z-Trp-Ser-OMe are obtained as a colourless powder.

Z-Zu-Leu-OMe 530 mg (1.5 mmol) of Z-Zu-OMe are dissolved in 4 ml MeOH, to which are added 1.6 ml 1N NaOH. After 5 min the saponification is concluded, 240 mg (1.6 mmol) HOBT are added, concentrated under vacuum and co-evaporated with toluene. The white residue is dissolved in 0.5 ml DMF, to which are added 326 mg (1.8 mmol) H-Leu-OMe.HCl, 4 ml THF, 0.20 ml (1.8 mmol) NMM and 310 mg (1.6 mmol) EDCI). The pH is set to 7 by addition of a few drops of NMM and stirring takes place for 16 hours at room temperature. The solvent is removed under vacuum and the crude product chromatographed on silica gel (mobile solvent $CHCl_3$: MeOH, 6:1, V:V). 700 mg (99%) of thin-layer chromatographically identical Z-Zu-Leu-OMe are obtained as a colourless oil.

Boc-Pro-Gly-NH$_2$ 0.56 mg (5 mmol) of H-Gly-NH$_2$.HCl are dissolved in 20 ml MeOH and 270 mg (5 mmol) NaOMe added. Stirring takes place for 10 min and the solvent is removed under vacuum. To the residue are added 15 ml DMF, 1.07 g (5 mmol) Boc-Pro-OH, 1.2 g (6.0 mmol) EDCI, 0.9 g (6 mmol) HOBT and 0.825 ml (7.5 mmol) NMM and stirring takes place for 16 hours. To the reaction mixture are added 10 g of mixed-bed ion exchanger (Merck ion exchanger V), stirring takes place for 0.5 hours, followed by filtering and washing with 10 ml MeOH. The filtrate is concentrated under vacuum, the resulting oil absorbed in 150 ml ethyl acetate and the organic phase washed three times with 10 ml 0.5N HCl, 10% NaHCO$_3$ solution and H$_2$O respectively.

The organic phase is dried with MgSO$_4$, the solvent distilled off under vacuum and the product precipitated out of ether. 0.66 g (49%) of thin-layer chromatographically identical product Boc-Pro-Gly-NH$_2$ is obtained as a colourless powder.

Z-Trp-Ser-Zu-Leu-OMe (See SEQUENCE ID NO: 9) 0.79 g (1.8 mmol) of Z-Trp-Ser-OMe are dissolved in a mixture of 2 ml THF and 2 ml MeOH. While stirring 2.0 ml (2.0 mmol) of 1N NaOH are added and stirred for 2 min. On completion of the saponification (TLC check) the reaction mixture is neutralized by the addition of 0.3 g (2.0 mmol) HOBT.

0.70 g (1.5 mmol) of Z-Zu-Leu-OMe are dissolved in 10 ml MeOH, 100 mg of 10% Pd/C catalyst are added and hydrated at room temperature with stirring under a hydrogen atmosphere for 0.5 hours. The catalyst is filtered off and washed with 5 ml MeOH. The filtrate is added to the neutralized reaction mixture from the saponification and the solvent is removed under vacuum. The residue is dissolved in a mixture of 3 ml DMF and 3 ml THF and at –10° C. 0.34 g (1.8 mmol) EDCI and 0.165 ml (1.5 mmol) NMM are added. After 15 hours the reaction is concluded by the addition of 10.0 g of mixed-bed ion exchanger (Merck ion exchanger V) and stirring takes place for 0.5 hours. The ion exchanger is filtered off and washed with MeOH, the filtrate concentrated under vacuum and chromatographed on silica gel (mobile solvent CHCl$_3$: MeOH, 9:1, V:V). 0.74 g (63%) of thin-layer chromatographically identical Z-Trp-Ser-Zu-Leu-OMe (See SEQUENCE ID NO: 4) are obtained as a colourless solid.

Fmoc-Arg(Pmc)-Pro-Gly-NH$_2$ (See SEQUENCE ID NO: 10) 540 mg (2.0 mmol) of Boc-Pro-Gly-NH$_2$ are dissolved in 5 ml abs. THF and mixed while stirring with 3 ml HCl/diethyl ether (abs. diethyl ether is for this saturated with hydrogen chloride at 0° C.). After 0.5 hours the solvent is removed under vacuum and co-evaporated three times with 5 ml toluene on each occasion.

110 mg (2.0 mmol) NaOMe are added to 5 ml abs. THF and after 5 min 5 ml DMF, 300 mg (2.0 mmol) HOBT and 1.32 g Fmoc-Arg(Pmc)-OH. Cooling to –10° C. takes place, 600 mg (3 mmol) EDCI are added and a pH of 7.0 is set with 0.33 ml NMM. After 15 hours of stirring the solvent is removed under vacuum, the resulting syrup absorbed in 150 ml ethyl acetate and the organic phase washed three times with 10 ml 0.5 N HCl, 10% NaHCO$_3$ solution and H$_2$O respectively. The organic phase is dried with MgSO$_4$, the solvent distilled off under vacuum and the product precipitated from hexane. 1.52 g (93%) of thin-layer chromatographically identical Fmoc-Arg(Pmc)-Pro-Gly-NH$_2$ are obtained as a colourless powder.

Z-Trp-Ser-Zu-Leu-Arg(Pmc)-Pro-Gly-NH$_2$ (See SEQUENCE ID NO: 12) 0.59 g (0.8 mmol) of Z-Trp-Ser-Zu-Leu-OMe are dissolved in a mixture of 1 ml THF and 2 ml MeOH. While stirring 1.0 ml (1.0 mmol) of 1N NaOH are added and stirred for 5 min. On completion of the saponification (TLC check) the reaction mixture is neutralized by the addition of 0.15 g (1.0 mmol) HOBT and the solvent is removed under vacuum. 0.62 g (0.76 mmol) of Fmoc-Arg-(Pmc)-Pro-Gly-NH$_2$ are dissolved in 5 ml CH$_2$Cl$_2$, 5 ml of dimethyl-ethylamine are added and stirring carried out overnight. The solvent is distilled off out of the reaction mixture under vacuum and the powdery residue absorbed in 3 ml DMF. The reaction mixture is evaporated to dryness and the residue dissolved in 3 ml DMF. The solution is added to the neutralized preparation from the saponification and 3 ml THF are added. At –10° C. 0.16 g (0.8 mmol) EDCI and 0.154 ml (1.4 mmol) NMM are added. After 8 hours the reaction mixture is concentrated under vacuum and chromatographed on silica gel (mobile solvent CHCl$_3$: MeOH, 4:1, V:V). 0.50 g (50%) of thin-layer chromatographically identical Z-Trp-Ser-Zu-Leu-Arg(Pmc)-Pro-Gly-NH$_2$ are obtained as a colourless solid.

pGlu-His(Trt)-Trp-Ser-Zu-Leu-Arg-(Pmc)-Pro-Gly-NH$_2$ (See SEQUENCE ID NO: 13) 162 mg (0.31 mmol) of pGlu-His(Trt)-OMe are dissolved in a mixture of 1 ml THF and 1 ml MeOH. While stirring 0.5 ml (0.5 mmol) of 1N NaOH are added and stirred for 0.5 hours. On completion of the saponification (TLC check) the reaction mixture is neutralized by the addition of 75 mg (0.5 mmol) HOBT.

367 mg (0.28 mmol) of Z-Trp-Ser-Zu-Leu-Arg(Pmc)-Pro-Gly-NH$_2$ (See SEQUENCE ID NO: 12) are dissolved in 5 ml MeOH, 50 mg of 10% Pd(C) catalyst are added and the mixture hydrated at room temperature with stirring under a hydrogen atmosphere for 0.5 hours. The catalyst is filtered off and washed with 5 ml MeOH. The filtrate is added to the neutralized reaction mixture from the saponification and the solvent is removed under vacuum. The residue is dissolved in a mixture of 1 ml DMF and 3 ml THF and at –10° C. 60 mg (0.31 mmol) EDCI and 33 ml (0.31 mmol) NMM are added. After 15 hours of stirring the reaction mixture is concentrated under vacuum and chromatographed on silica gel (mobile solvent CHCl$_3$: MeOH, 4:1, V:V). 0.31 g (63%) of thin-layer chromatographically identical pGlu-His(Trt)-Trp-Ser-Zu-Leu-Arg-(Pmc)-Pro-Gly-NH$_2$ (see SEQUENCE ID NO: 13) are obtained as a colourless solid.

pGlu—His—Trp—Ser—Zu—Leu—Arg—Pro—Gly—NH$_2$.2 TFA D-22677 (See SEQUENCE ID NO: 13)

Relative molecular mass 1379.45 g/mol 0.20 g (0.13 retool) of pGlu-His(Trt)-Trp-Ser-Zu-Leu-Arg-(Pmc)-Pro-Gly-NH$_2$ (See SEQUENCE ID NO: 13) are dissolved in a previously manufactured mixture of 8.25 g TFA, 0.5 g H$_2$O, 0.5 g phenol, 0.5 g thioanisole and 0.25 g methanethiol and stirred carried out for 4 hours at room temperature. The reaction mixture is added to a mixture of 200 ml diethyl ether and 50 ml hexane, in the course of which the peptide precipitates. The latter is filtered off and washed with diethyl ether. The peptide is purified by RP chromatography (HPLC, Nucleosil-gel, flow 6 ml/min, CH$_3$CN/H$_2$O with 0.1% TFA, gradient 20% CH$_3$CN to 60% CH$_3$CN in 30 min). The product is precipitated from ether-hexane after the separation. 120 mg (0.087 mmol, 67%) of product are obtained in the form of a colourless powder.

FAB-MS: 1151.6 (M+H$^+$), relative molecular mass given above −2.TFA.

Preparation of the LHRH antagonist Ac-D-(2-Nal)-p-Cl-D-Phe-D-(3-pal)-Ser-Tyr-Zu-Leu-Arg(TFA)-Pro-D-Ala-NH$_2$ D-23010 derived from cetrorelix The synthesis is carried out in liquid phase. The peptide couplings are activated with EDCI/HOBT or HOOBT. The protected sugar amino acid is abbreviated to Z-Zu-OMe as in the previous example.

Synthesis strategy (See SEQUENCE ID NOs: 14 and 15):

Ac—D—(2-Nal)-p-Cl—D—Phe—D—(3-Pal)/Ser—Tyr/Zu/Leu/Arg(HCl)—Pro—D—Ala—NH$_2$
Ser—Tyr—Zu—Leu(residues 5–8 of SEQUENCE ID NO: 14)

Ac—D—(2-Nal)-p-Cl—D—Phe—D—(3-Pal)—Ser—Tyr—Zu—Leu(residues 1–7 of SEQUENCE ID NO: 15)
Ac—D—(2-Nal)-p-Cl—D—Phe—D—(3-Pal)—Ser—Tyr—Zu—Leu—Arg(TFA)—Pro—D—Ala—NH$_2$ Z—Ser—Tyr—OET 0.72 g (3 mmol) of Z-Ser-OH, 0.74 g (3 mmol) of H-Tyr-OET.HCl, 0.68 g (3.6 mmol) EDCI, 0.58 g (3.6 mmol) HOBT and 0.66 ml (6 mmol) NMM are dissolved at −10° C. in 8 ml DMF and stirred for 15 hours at room temperature. The DMF is distilled off under vacuum, the residue dissolved in 50 ml ethyl acetate and the organic phase washed three times with 10 ml 0.5 N HCl, 10% NaHCO$_3$ solution and H$_2$O respectively. The organic phase is dried with MgSO$_4$ and the solvent distilled off under vacuum. 1.21 g (94%) of thin-layer chromatographically identical Z-Ser-Tyr-OET are obtained as a colourless solid.

The synthesis of Z-Zu-Leu-OMe is described in the previous example.

Z-Ser-Tyr-Zu-Leu-OMe (See SEQUENCE ID NO: 16) 0.32 g (0.75 mmol) of Z-Ser-Tyr-OEt are dissolved in a mixture of 2 ml THF and 2 ml MeOH. While stirring 1.0 ml (1.0 mmol) of lN NaOH are added and stirred for 5 min. On completion of the saponification (TLC check) the reaction mixture is neutralized by the addition of 0.15 g (1.0 mmol) HOBT.

0.24 g (0.5 mmol) of Z-Zu-Leu-OMe are dissolved in 5 ml MeOH, 50 mg of 10% Pd/C catalyst are added and the mixture hydrated at room temperature with stirring under a hydrogen atmosphere for 0.5 hours. The catalyst is filtered off and washed with 5 ml MeOH. The filtrate is added to the neutralized reaction mixture from the saponification and the solvent is removed under vacuum. The residue is dissolved in a mixture of 2 ml DMF and 2 ml THF and at −10° C. 0.15 g (0.75 mol) EDCI and 0.11 ml (1.0 mmol) NMM are added. After 15 hours the reaction solution is concentrated under vacuum and chromatographed on silica gel (mobile solvent CHCl$_3$: MeOH, 6:1, V:V). 0.26 g (72%) of thin-layer chromatographically identical Z-Ser-Tyr-Zu-Leu-OMe are obtained as a colourless solid.

Ac-D-(2-Nal)-p-Cl-D-Phe-D-(3-Pal)-Ser-Tyr-Zu-Leu-OMe (See SEQUENCE ID NO: 17) 145 mg (0.2 mmol) of Z-Ser-Tyr-Zu-Leu-OMe are dissolved in 5 ml MeOH and Pd/C catalyst (10%) is stirred in for 0.5 hours under a hydrogen atmosphere with a spatula tip. The catalyst is filtered off, washed with MeOH and the filtrate evaporated to dryness under vacuum. The residue is dissolved in 3 ml DMF, 180 mg (0.3 mmol) Ac-D-Nal-D-p-Cl-Phe-D-Pal-OH added, 60 mg (0.3 mmol) EDCI, 45 mg (0.3 mmol) HOOBT and 33 µl (0.3 mmol) NMM added and stirring carried out overnight. The reaction mixture is concentrated under high vacuum and the residue chromatographed on silica gel (mobile solvent: CHCl$_3$/MeOH 4:1). 187 mg (80%) of chromatographically identical Ac-D-(2-Nal)-p-Cl-D-Phe-D-(3-Pal)-Ser-Tyr-Zu-Leu-OMe are obtained as a colourless hard foam.

Ac-D-(2-Nal)-p-Cl-D-Phe-D-(3-Pal)-Ser-Tyr-Zu-Leu-Arg-(TFA)-Pro-D-Ala-NH$_2$ D-23010

187 mg (0.2 mmol) of Ac-D-(2-Nal)-p-Cl-D-Phe-D-(3-Pal)-Ser-Tyr-Zu-Leu-OMe are added to 2 ml MeOH and 2 ml THF and 0.3 ml 1N NaOH, followed by stirring for 0.5 hours at room temperature. If the saponification has been completed (TLC check), a PH of 4–5 is set by the addition of HOOBT and concentration under vacuum takes place. The residue is dissolved in 2 ml DMF, 110 mg (0.3 mmol) H-Arg(HCl)-Pro-D-Ala-NH$_2$ and 60 mg (0.3 mmol) EDCI are added and stirring carried out overnight. (The pH of the reaction solution should come to 5).

The reaction mixture is concentrated under vacuum and the residue chromatographed on silica gel (mobile solvent CH$_3$CN/H$_2$O, 4:1). 240 mg (80%) of chromatographically largely identical product are obtained, which are converted into hydrochloride by the addition of a small amount of HCl. The further purification is carried out by RP chromatography (HPLC, Nucleosil-gel), flow 6 ml/min, CH$_3$CN/H$_2$O with 0.1% TFA, gradient 35% CH$_3$CN to 40% CH$_3$CN, in 30 min). The product is freeze-dried from t-butanol. 90 mg (0.060 mmol, 30%) of product are obtained as trifluoroacetate in the form of a colourless powder.

We claim:

1. A compound comprising a D-glucopyranuronic acid having the formula:

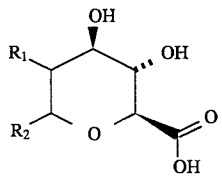

where
R$^1$ signifies OH, NH$_2$, NH-CO-O-CH$_2$-C$_6$H$_5$, NH-CO-O-tert.butyl, or NH-CO-CH$_3$ R$^2$ signifies CH$_2$-NH$_2$, OH, OCH$_3$, OCH$_2$-C$_6$H$_5$, CH$_2$-NH-CO-O-CH$_2$-C$_6$H$_5$, CH$_2$-NH-CO-O-tert.butyl or CH$_2$-NH-CO-CH$_3$, or its enantiomer incorporated into a pharmacologically active peptide or its salt.

2. 7-amino-L-glycero-L-gulo-2,6-anhydro-7-desoxy-heptonic acid with the formula

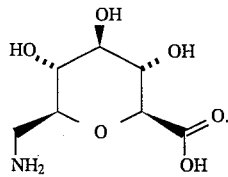

3. Method for manufacturing 7-amino-L-glycero-L-gulo-2,6-anhydro-7-desoxy-heptonic acid comprising the steps of:

a) reducing β-D-glucopyranosyl nitromethane with hydrogen on a palladium catalyst and then reacting resulting reduced β-D-glucopyranosyl nitromethane with chloroformic acid benzyl ester;

b) oxidizing N-benzoxycarbonyl-β-D-glucopyranosyl methylamine with oxygen on a platinum catalyst and then esterifying resulting oxidized N-benzoxycarbonyl-β-D-glucopyranosyl methylamine with alcohol;

c) and splitting protective groups of the 7-benzoxycarbonylamino-L-glycero-L-gulo- 2,6-anhydro-7-desoxy-heptonic acid methyl ester formed as a result of steps a) and b).

4. 7-benzoxycarbonylamino-L-glycero-L-gulo-2,6-anhydro-7-desoxy-heptonic acid methyl ester.

5. 7-acetylamino-L-glycero-L-gulo-2,6-anhydro-7-desoxy-heptonic acid methyl ester.

6. 2-benzoxycarbonylamino-O$^1$-methyl-2-desoxy-β-D-glucopyranuronic acid

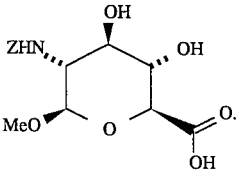

7. A composition comprising 7-amino-L-glycero-L-gulo-2,6-anhydro-7-desoxyheptonic acid or 7-amino-D-glycero-D-gulo-2,6-anhydro-7-desoxy-heptonic acid incorporated into a pharmacologically active peptide or its salt.

8. A composition comprising a 2-benzoxycarbonylamino-O$^1$-methyl-2-desoxy-β-D-glucopyranuronic acid or 2-benzoxycarbonylamino-$O^1$-methyl-2-desoxy-α-D-gluco-pyranuronic acid incorporated into a pharmacologically active peptide or its salt.

9. Pharmacologically active peptides or their salts containing as a structural element 7-amino-L-glycero-L-gulo-2,6-anhydro-7-desoxy-heptonic acid.

10. Pharmacologically active peptides or their salts containing as a structural element 2-benzyloxycarbonyl-amino-$O^1$-methyl-2-desoxy-D-glucopyranuronic acid.

11. Ac-D-(2-Nal)-p-Cl-D-Phe-D-(3-Pal)-Ser-Tyr-D-Lys-(Zu)-Leu-Arg-Pro-D-Ala-NH$_2$×TFA, wherein Zu=7-amino-L-glycero-L-gulo-2,6-anhydro-7-desoxy-heptonic acid, and TFA=trifluoroacetate.

12. pGlu-His-Trp-Ser-Zu-Leu-Arg-Pro-Gly-NH$_2$ (See SEQUENCE ID NO: 4)×2TFA, wherein Zu and TFA signify as in the preceding claim.

13. Ac-D-(2-Nal)-p-Cl-D-Phe-D-(3-Pal)-Ser-Tyr-Zu-Leu-Arg(TFA)-Pro-D-Ala-NH$_2$, wherein Zu and TFA signify as in the preceding claim.

14. Ac-D-(2-Nal)-p-Cl-D-Phe-D-(3-Pal)-Ser-Zu-Leu-Arg-(TFA)-Pro-D-Ala-NH$_2$, wherein Zu and TFA signify as in the preceding claim.

15. A composition suitable for use as a medicament comprising a compound according to any one of claims 11, 12, 13 or 14 and a pharmacologically active peptide or its salt.

* * * * *

SEQUENCE LISTING ( 1 ) GENERAL INFORMATION:

( i i i ) NUMBER OF SEQUENCES: 17

( 2 ) INFORMATION FOR SEQ ID NO:1:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:1:

```
Xaa  Tyr  Trp  Lys  Val
1                    5
```

( 2 ) INFORMATION FOR SEQ ID NO:2:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:2:

```
Xaa  Phe  Trp  Lys  Thr
1                    5
```

( 2 ) INFORMATION FOR SEQ ID NO:3:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:3:

```
Xaa  Phe  Xaa  Ser  Tyr  Lys  Xaa  Leu  Arg  Pro  Ala
1                    5                         10
```

( 2 ) INFORMATION FOR SEQ ID NO:4:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:4:

```
Glu  His  Trp  Ser  Xaa  Leu  Arg  Pro  Gly
1                    5
```

( 2 ) INFORMATION FOR SEQ ID NO:5:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:5:

```
Xaa  Phe  Xaa  Ser  Tyr  Xaa  Leu  Arg  Pro  Ala
1                  5                        10
```

( 2 ) INFORMATION FOR SEQ ID NO:6:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:6:

```
Lys  Thr  Xaa  Phe  Trp
1                  5
```

( 2 ) INFORMATION FOR SEQ ID NO:7:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:7:

```
Glu  His  Trp  Ser  Xaa  Leu  Arg  Pro  Gly
1                  5
```

( 2 ) INFORMATION FOR SEQ ID NO:8:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:8:

```
Glu  His  Trp  Ser  Xaa  Leu  Arg  Pro  Gly
1                  5
```

( 2 ) INFORMATION FOR SEQ ID NO:9:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:9:

```
Trp  Ser  Xaa  Leu
1                  5
```

( 2 ) INFORMATION FOR SEQ ID NO:10:

( i ) SEQUENCE CHARACTERISTICS:
        ( A ) LENGTH: 3 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:10:

Arg Pro Gly
1

( 2 ) INFORMATION FOR SEQ ID NO:11:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:11:

Xaa Phe Xaa Ser Xaa Leu Arg Pro Ala
1               5

( 2 ) INFORMATION FOR SEQ ID NO:12:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:12:

Trp Ser Xaa Leu Arg Pro Gly
1               5

( 2 ) INFORMATION FOR SEQ ID NO:13:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:13:

Glu His Trp Ser Xaa Leu Arg Pro Gly
1               5

( 2 ) INFORMATION FOR SEQ ID NO:14:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:14:

Xaa Phe Xaa Ser Tyr Xaa Leu Arg Pro Ala
1               5

( 2 ) INFORMATION FOR SEQ ID NO:15:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear (i i) MOLECULE TYPE: peptide (x i) SEQUENCE DESCRIPTION: SEQ ID NO:15:

Xaa Phe Xaa Ser Tyr Xaa Leu Arg Pro Ala
1               5

(2) INFORMATION FOR SEQ ID NO:16:

(i) SEQUENCE CHARACTERISTICS:
    (A) LENGTH: 4 amino acids
    (B) TYPE: amino acid
    (C) STRANDEDNESS: single
    (D) TOPOLOGY: linear (i i) MOLECULE TYPE: peptide (x i) SEQUENCE DESCRIPTION: SEQ ID NO:16:

Ser Tyr Xaa Leu
1

(2) INFORMATION FOR SEQ ID NO:17:

(i) SEQUENCE CHARACTERISTICS:
    (A) LENGTH: 7 amino acids
    (B) TYPE: amino acid
    (C) STRANDEDNESS: single
    (D) TOPOLOGY: linear (i i) MOLECULE TYPE: peptide (x i) SEQUENCE DESCRIPTION: SEQ ID NO:17:

Xaa Phe Xaa Ser Tyr Xaa Leu
1               5